United States Patent [19]

Dickhudt

[11] 4,432,377

[45] Feb. 21, 1984

[54] BIOMEDICAL LEAD WITH RING ELECTRODE AND METHOD OF MAKING SAME

[75] Inventor: Eugene A. Dickhudt, New Brighton, Minn.

[73] Assignee: Medtronic, Inc., Minneapolis, Minn.

[21] Appl. No.: 344,125

[22] Filed: Jan. 29, 1982

[51] Int. Cl.³ .............................................. A61N 1/04
[52] U.S. Cl. ................................ 128/786; 128/419 P; 29/863
[58] Field of Search .............................. 128/784–786, 128/419 P, 642; 29/861, 863

[56] References Cited

U.S. PATENT DOCUMENTS

| | | | |
|---|---|---|---|
| 3,769,984 | 11/1973 | Muench | 128/419 P X |
| 4,033,357 | 7/1977 | Helland et al. | 128/785 |
| 4,280,511 | 7/1981 | O'Neill | 128/784 |

FOREIGN PATENT DOCUMENTS 2421626 12/1979 France ................................. 128/786

Primary Examiner—Lee S. Cohen
Attorney, Agent, or Firm—Robert J. Klepinski; John L. Rooney; Joseph F. Breimayer

[57] ABSTRACT

A body implantable lead having a barrel-shaped ring electrode with the ends of the barrel embedded into the lead casing material. A cylindrical flange within the bore of the ring electrode contacts the lead conductor. The lead and electrode are formed by placing the lead in a press with the electrode between a pair of collets with elliptical working surfaces and the lead casing and conductor passing through the axial bore of the collets, and forcing the collets together to shape the electrode and to force the ends of the ring into the casing and the flange into contact with the lead conductor.

8 Claims, 5 Drawing Figures

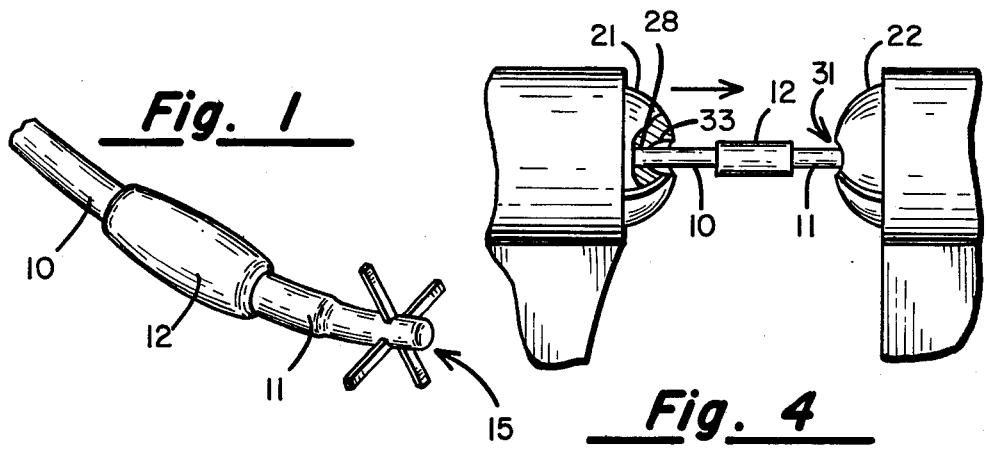
Fig. 1
Fig. 4
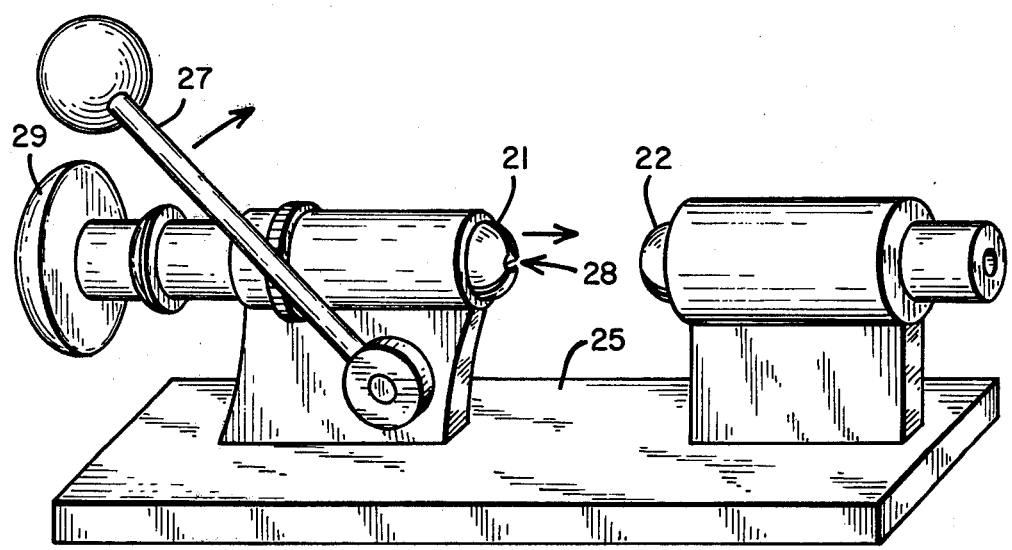
Fig. 2
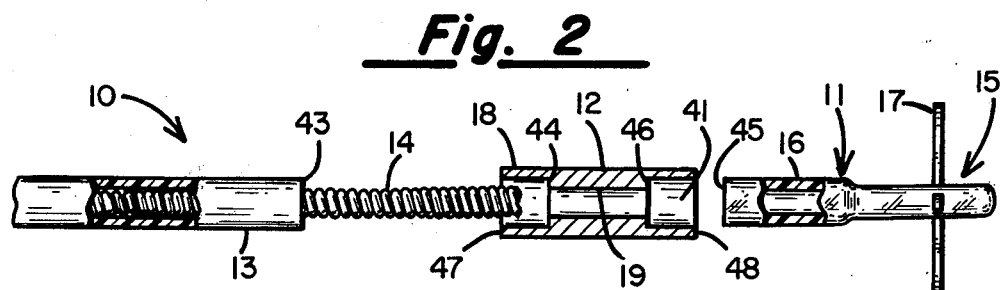
Fig. 3
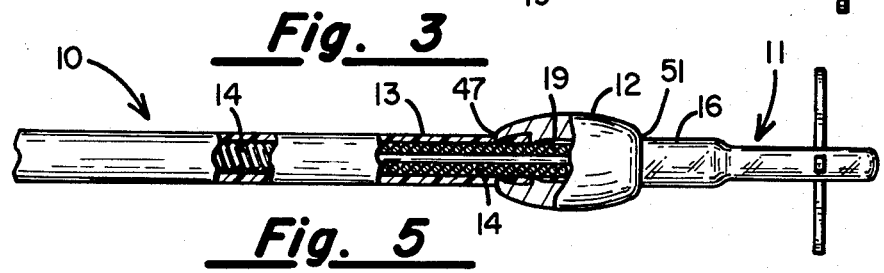
Fig. 5

BIOMEDICAL LEAD WITH RING ELECTRODE AND METHOD OF MAKING SAME

BACKGROUND OF THE INVENTION

1. Field of the Invention

This invention, in general, relates to the field of body implantable leads for the electrical stimulation of living tissue, and more particularly concerns a lead having a ring electrode with a barrel shape for improved contact with body tissue which, at the same time, functions to mechanically weld the various parts of the lead together and which can be made in a simplified manufacturing process.

2. Description of the Prior Art

Electrical stimulation of the body is an increasingly important medical procedure. For example, electrical stimulation of the heart is now the preferred medical procedure for treating heart block, as well as other types of heart malfunction, and electrical stimulation of the spinal cord has proven to be effective in relieving chronic pain. Generally the leads used in such biomedical stimulation contexts comprise an exposed electrode for making electrical contact with the body tissues and a lead body, which includes a conductor electrically connected to the electrode and an insulating casing enclosing the conductor and forming the external portion of the lead body. Generally, the casing is made of a pliable material generally inert to body fluids, such as polyurethane, silicone rubber or the like.

The electrode in many of such lead applications comprises a conducting band encircling the lead body and conventionally is called a ring electrode. Generally such an electrode is of the form of a right-circular cylinder made of platinum or any similar material which is highly conductive and resistant to body fluid. Examples of such ring electrodes are disclosed in U.S. Pat. No. 4,280,511 for a Ring Electrode for Pacing Lead and Process of Making Same invented by Edward G. O'Neill and U.S. Pat. No. 4,328,812 entitled Ring Electrode for Pacing Lead and an invention of Keith A. Ufford and Edward G. O'Neill, U.S. Pat. No. 4,328,812 discloses a ring electrode in which the diameter of the ring cylinder is greater than the diameter of the lead casing (except for a small portion of the casing adjacent the electrode which has the same diameter as the ring electrode). This places the surface of the ring in closer relation to the body tissue than the casing is generally, thereby improving electrical contact with the tissue. However, in order to ensure that body fluids do not penetrate the juncture of the ring electrode and the lead body, and to ensure good electrical connection between the electrode and conductor, the structure of the electrical connection is quite complex. U.S. Pat. No. 4,280,511 shows a simplified ring structure and a simplified method of manufacture of the lead with the ring electrode. The diameter of the ring electrode in this latter disclosure is the same as the diameter of the lead body.

SUMMARY OF THE INVENTION

It is an object of the invention to provide a body implantable lead with a ring electrode in which the junction between the ring electrode and the insulating lead casing is smooth and without snags which could traumatize body tissue.

It is a further object of the invention to provide a lead in which the juncture between the ring electrode and the insulating casing is well-sealed against the penetration of body fluids.

In addition, it is an object of the invention to provide a body implantable lead in which the ring electrode, at its maximum diameter, has a larger diameter than all portions of the lead casing in the neighborhood of the electrode, thereby improving electrical contact between the electrode and body tissue.

It is a further object of the invention to provide a ring electrode with an improved means for making electrical contact with the conductor.

It is another object of the invention to provide a body implantable lead in which the ring electrode also acts as a means for holding together the proximal and distal portions of the lead body casing, and the conductor to both portions of the casing.

It is a further object of the invention to provide a body implantable lead with a ring electrode which functions to mechanically weld a lead anchoring means to the other portions of the lead body.

Finally, it is an object of the invention to provide a manufacturing process for making a lead with one or more of the above characteristics in a simplified, efficient, and cost-effective manner.

The method of manufacture, according to the invention, provides for a body implantable lead of the type having an exposed ring electrode, a lead body comprising a conductor electrically connected to the electrode, and an insulating casing enclosing the conductor and forming the external portion of the lead body, the casing being of a pliable material generally inert to body fluids, and includes the steps of slipping the casing and the conductor into the ring electrode, and forcing the ends of the ring inward until they embed themselves into the casing. Preferably the step of forcing also comprises pressing the ring electrode into a barrel shape; "barrel" within the context of this invention means a barrel having a bulge, i.e., the barrel has a maximum diameter occurring at a location between the ends of the barrel.

The preferred ring electrode includes an internal flange which preferably is in the form of a cylindrical rib protruding into the axial bore of the ring, and in the preferred method of manufacture the step of forcing includes compressing at least a portion of the flange inward until it contacts the conductor.

Numerous other features, objects and advantages of the invention will become apparent from the following detailed description when read in conjunction with the accompanying drawings.

BRIEF DESCRIPTION OF THE DRAWINGS

In the drawing:

FIG. 1 is a perspective view of an exemplary body implantable lead according to the invention;

FIG. 2 is a perspective view of the press in which the electrode is shaped and attached to the lead body and conductor;

FIG. 3 is a partially cutaway side view of the lead of FIG. 1 in a dismantled stage, just prior to the electrode being slipped over the lead body and conductor;

FIG. 4 shows the lead body and electrode in position in the press of FIG. 2 in the process of manufacture; and FIG. 5 is a partially cutaway side view of the manufactured lead of FIGS. 1 and 3.

DESCRIPTION OF THE PREFERRED EMBODIMENT

A lead according to the invention is shown in FIG. 1. The lead includes a proximal portion 10 of the lead body 10, a distal portion 11 of the lead body, an exposed ring electrode 12, and a lead anchoring means 15 which is integrally formed with the distal portion 11 of the lead body. In the context of leads the proximal portion of the lead is the portion closest to the pulse generator and the distal portion is that part farthest from the pulse generator. The major part of the proximal portion 10 of the lead body would extend some distance to the left in the drawing and ultimately be connected to source of an electrical pulse; this part is conventional and is not shown. The ring electrode 12 transmits the electrical pulse to the body tissue in which the lead is implanted and is a principle feature of the present invention.

A press for use in shaping the electrode and making the lead is shown in FIG. 2. A pair of collets 21 and 22 are opposed on a frame 25. At least one of the collets 21, is movable in the direction of the other collet 22 by means of a lever 27. The axial bore 28 (best seen in FIG. 4) of collet 21 is adjustable by means of knob 29. The press shown is a conventional jewelers lathe made by Louis Levine and Son, Inc. of 3573 Hayden Ave., Culver City, Calif., 90230 which has been modified as discussed above and as shown in the drawing.

A preferred embodiment of a lead according to the invention prior to assembly is shown in FIG. 3. Ring electrode 12 is shown centered between the proximal portion 10 of the lead body and the distal portion 11 of the lead body. The proximal portion 10 of the lead body comprises insulating casing 13 and conductor 14. The distal portion 11 of the lead body includes casing 16 integrally formed with lead anchoring means 15. The lead anchoring means 15 shown includes tines such as 17 and will not be discussed further herein since the particular type of lead anchoring means is not a feature of the invention. The preferred embodiment of ring electrode 12 comprises a cylinder 18 having an internal flange 19. Flange 19 preferably comprises a cylindrical rib 19 which protrudes into the bore 41 of the cylinder 18 of the electrode 12.

The lead according to the invention is manufactured by first slipping casings 13 and 16 and conductor 14 into ring 12. Preferably the casings 13 and 16 and conductor 14 are slipped into electrode 12 with end 43 of the proximal portion 13 of the casing abutting a first side 44 of flange 19 and end 45 of the distal portion 16 of the casing abutting the side 46 of flange 19 opposite first side 44. Preferably conductor 14 is slipped entirely through the length of electrode 12 so that a portion of it extends into distal portion 16 of the casing. The lead, thus assembled, is then placed in the collets 21 and 22 of the press as shown in FIG. 4. The lead is placed so that the proximal portion 10 of the lead body lies within the axial bore 28 of collet 21 and distal portion 11 lies in the axial bore 31 of collet 22 with the electrode 12 lying between the collets. Collet 21 is partially cut away in FIG. 4 so that the preferred eliptical shape of the working surface 33 of the collet can be seen. Lever arm 27 (FIG. 2) of the press is then moved forward forcing collet 21 toward collet 22 compressing ring electrode 12 between the working surfaces, such as 28, which forces the ends 47 and 48 (see FIG. 3) of cylinder 18 of ring 12 inward until they embed themselves into the material of the proximal portion 13 of the casing and distal portion 16 of the casing respectively. The compression of ring 12 between collets 21 and 22 also shapes ring 12 into the barrel form and forces flange 19 downward into electrical and mechanical contact with conductor 14. The force of the press is such that a firm mechanical weld is formed between ends 47 and 48 and casings 13 and 16 respectively and between flange 19 and conductor 14.

A preferred embodiment of a lead according to the invention, as manufactured according to the invention, is shown in FIG. 5 in partially cutaway view. Cylinder 18 has now become barrel-shaped and end 47 of cylinder 18 is embedded within the material of proximal portion 13 of the casing. Similarly, end 48 of cylinder 18 is embedded in the material of the distal portion 16 of the casing. Flange 19 is pressed firmly into conductor 14.

The materials of the invention are conventional, with the electrode being made of platinum or any other good conductor which is resistant to body fluids, the casing 13 and 16 being made of polyurethane, silicone rubber or any other pliable material which is generally inert to body fluids. Conductor 14 is a conventional coil conductor made of platinum or other suitable conducting material. Collets 21 and 22 are made of hardened tooled steel such as that sold under the trademark Stentor TM.

In the preferred embodiment of the invention, cylinder 18 has an external diameter of 0.046 inches and an internal diameter of 0.035 inches with the internal diameter of flange 19 being 0.0225 inches. Conductor 14 has an external diameter of about 0.022 inches. The tubing forming casing 13 and 16 has an inner diameter of from 0.020 inches to 0.025 inches and an outside diameter of about 0.035 inches. After compression, the ends 47 and 48 of ring electrode 12 are reduced to a diameter of approximately 0.030 inches so that they extend approximately 0.005 inches beneath the surface of casing 13 and 16. In practice, materials such as the casing 13 and 16 may be received in slightly larger sizes, since the sizes specified are for small leads such as those used in the epidural space and such small tolerances are not always achieved by vendors. In this case the casing such as 13 and 16 may be swaged down to the appropriate sizes before they are slipped into ring electrode 12.

A feature of the invention is that the joints, such as at 51, between the casing such as 16 and the ring electrode 12, are smooth. The lead may be passed smoothly through body tissue without the joints, such as 51, catching and causing possible trauma.

Another feature of the invention is that the electrode 12 over its entire exposed surface is of a greater diameter than any portion of the casings 13 and 16 in the immediate neighborhood of electrode 12. Thus, the electrode 12 makes excellent contact with body tissue, and the neighboring casings 13 and 16 and any fibrosis formed by the body about the casings 13 and 16 causes minimal interference with the electrical contact.

A further feature of the invention is that the electrode 12 firmly connects proximal portion 13 and distal portion 16 to one another and also firmly connects conductor 14 to both portions 13 and 16 of the casing. This connection is made simply without any of the complexity and/or need for sealing materials such as used in the prior art.

Another feature of the invention is that the seal between the electrode 12 and the casing such as 16 is highly resistant to penetration by body fluids, without the use of medical epoxy and other sealants used in the prior art.

It is an important feature of the invention that all of the above features are obtained with unusually simple electrode construction and manufacturing process.

There has been described a novel body implantable lead and process for manufacturing the lead that provides a relatively inexpensive lead of very high quality. While the invention has been described in connection with a particular embodiment, one skilled in the art will appreciate that numerous other embodiments and departures from the embodiment shown may be made without departing from the inventive concepts. For example, "barrel" shapes, other than elliptical may be used. The invention may be used in combination with a wide range or varieties of lead anchoring means. Flange 19 may take forms other than the single cylindrical rib shape shown. A wide variety of dimensions for the elements such as the ring electrode 12 may be chosen by those skilled in the art to arrive at the desired characteristics as described. In addition, other features may be added to the lead, or the lead might be employed in areas of the body other than those expressly mentioned, while still employing the inventive elements. It is therefore to be understood that, within the scope of the appended claims, the invention may be practiced other than has been specifically described.

What is claimed is:

1. A method of making a body implantable lead of the type having an exposed ring electrode, a lead body comprising a conductor electrically connected to said electrode and an insulating casing enclosing said conductor and forming the external portion of said lead body, said casing being of a pliable material generally inert to body fluids, comprising the steps of:
   slipping said casing and said conductor into said ring electrode so that the conductor is electrically connected to the ring electrode; and
   forcing ends of said ring inward until they embed themselves into said casing.

2. A method as in claim 1 wherein said step of forcing also comprises pressing said ring into a barrel shape.

3. A method as in claim 1 where in said ring electrode includes an internal flange and said step of forcing further comprises compressing at least a portion of said flange inward until it contacts said conductor.

4. A method as in claim 3 wherein said flange comprises a cylindrical rib protruding into the axial bore of said ring, said insulating casing includes a proximal portion and a distal portion, and said step of slipping further comprises:
   abutting said proximal portion of said casing against a first side of said rib; and
   abutting said distal portion against the side of said rib opposite said first side.

5. A method as in claim 1 wherein said step of forcing comprises the steps of:
   placing said lead in a press having a pair of collets with elliptically shaped working surfaces and having an axial bore, with said lead body within the axial bore and said ring between said collets with the working surfaces of said collets engaging said ring; and
   forcing said collets together to shape said ring and drive the ends of the ring into the casing.

6. A body implantable lead of the type having an exposed ring electrode, a lead body comprising a conductor electrically connected to said electrode and a casing enclosing said conductor and forming the external portion of said lead body, said casing being of a pliable material generally inert to body fluids, wherein said electrode comprises a conductive cylinder having ends embedded in the material of the casing to form a barrel, the barrel having a maximum diameter between the ends of said barrel greater than the diameter of said casing, and the embedded ends of said conductive barrel having a diameter less than the diameter of said casing.

7. A lead as in claim 6 wherein said ring electrode further comprises a cylindrical flange protruding into the axial bore of said cylinder and contacting said conductor.

8. A lead as in claim 7 wherein said casing includes a proximal portion and a distal portion and wherein said proximal portion abuts against a first side of said flange and said distal portion abuts against the side opposite said first side of said flange.

* * * * *